United States Patent
Hauger et al.

(10) Patent No.: US 9,958,392 B2
(45) Date of Patent: May 1, 2018

(54) OPTICAL FILTER SYSTEM AND FLUORESCENCE OBSERVATION SYSTEM

(71) Applicant: Carl Zeiss Meditec AG, Jena (DE)

(72) Inventors: Christoph Hauger, Aalen (DE); Roland Guckler, Ulm (DE); Marco Wilzbach, Stuttgart (DE); Helge Jess, Oberkochen (DE); Selamawit Getachew Kelemu, Aalen (DE); Holger Matz, Unterschneidheim (DE)

(73) Assignee: CARL ZEISS MEDITEC AG, Jena (DE)

( * ) Notice: Subject to any disclaimer, the term of this patent is extended or adjusted under 35 U.S.C. 154(b) by 73 days.

(21) Appl. No.: 14/722,265

(22) Filed: May 27, 2015

(65) Prior Publication Data

US 2015/0346098 A1 Dec. 3, 2015

(30) Foreign Application Priority Data

May 27, 2014 (DE) .......... 10 2014 008 243

(51) Int. Cl.
*G01N 21/64* (2006.01)
*G02B 5/22* (2006.01)
(Continued)

(52) U.S. Cl.
CPC ......... *G01N 21/6458* (2013.01); *G02B 5/208* (2013.01); *G02B 5/22* (2013.01);
(Continued)

(58) Field of Classification Search
CPC ........... G01N 21/6458; G01N 21/6445; G01N 21/64; G01N 21/6428; G01N 21/6456;
(Continued)

(56) References Cited

U.S. PATENT DOCUMENTS

| 5,127,730 A | 7/1992 | Brelje et al. |
| 6,212,425 B1 | 4/2001 | Irion et al. |

(Continued)

FOREIGN PATENT DOCUMENTS

| DE | 691 31 176 T2 | 2/1992 |
| DE | 195 48 913 A1 | 7/1997 |

(Continued)

OTHER PUBLICATIONS

Erdogan T. "Optical Filters for Wavelength Selection in Fluorescence Instrumentation" Apr. 2011, John Wiley & Sons, Inc., Current Protocols in Cytometry, pp. 2.4.1-2.4.25.*
(Continued)

*Primary Examiner* — Marin Pichler
(74) *Attorney, Agent, or Firm* — Patent Portfolio Builders PLLC

(57) ABSTRACT

An optical filter system for florescence observation comprises an illumination light filter (I) and an observation light filter (O). The observation light filter has plural transmitting regions ($D_1^O, D_2^O$) allowing fluorescent light to traverse the observation light filter. Blocking regions ($S_0^O, S_1^O$) separate the transmitting regions. The illumination light filter has transmitting regions ($D_0^I, D_1^I$) where the observation light filter has a corresponding blocking region. The illumination light filter has blocking regions ($S_1^I, S_2^I$) where the observation light filter has a corresponding transmitting region. The plural transmitting regions of the illumination light filter hallow for an improved color impression in the normal light observation.

7 Claims, 4 Drawing Sheets

(51) Int. Cl.
*G02B 21/00* (2006.01)
*G02B 21/16* (2006.01)
*G02B 5/20* (2006.01)

(52) U.S. Cl.
CPC ......... *G02B 21/0076* (2013.01); *G02B 21/16* (2013.01); *G01N 2021/6471* (2013.01)

(58) Field of Classification Search
CPC ... G01N 2021/6471; G01N 2021/6417; G01N 2021/6419; G01N 2021/6421; G01N 2021/6423; G01N 2021/6439; G02B 5/208; G02B 5/22; G02B 5/28; G02B 21/0076; G02B 21/16; G02B 2207/113
See application file for complete search history.

(56) References Cited

U.S. PATENT DOCUMENTS

| 6,899,675 | B2 | 5/2005 | Cline et al. | |
|---|---|---|---|---|
| 2001/0046673 | A1 | 11/2001 | French et al. | |
| 2004/0109231 | A1 | 6/2004 | Haisch et al. | |
| 2006/0004292 | A1 | 1/2006 | Beylin | |
| 2006/0186349 | A1* | 8/2006 | Weiss | G01N 1/286 250/486.1 |
| 2007/0090985 | A1* | 4/2007 | Jess | G01N 21/6428 341/155 |
| 2010/0044583 | A1 | 2/2010 | Steffen et al. | |
| 2011/0149084 | A1 | 6/2011 | Beck et al. | |
| 2012/0057226 | A1 | 3/2012 | Kuster | |
| 2012/0300294 | A1 | 11/2012 | Jess et al. | |
| 2013/0307953 | A1* | 11/2013 | Hauger | A61B 5/0071 348/71 |

FOREIGN PATENT DOCUMENTS

| DE | 103 39 784 A1 | 3/2004 | |
|---|---|---|---|
| DE | 10 2005 005 253 A1 | 11/2005 | |
| DE | 10 2006 015 272 A1 | 10/2007 | |
| DE | 10 2008 034 008 A1 | 1/2010 | |
| DE | 10 2009 058 663 A1 | 6/2011 | |
| DE | 10 2010 033 825 A1 | 2/2012 | |
| DE | 10 2010 044 503 A1 | 3/2012 | |
| WO | 2004/054439 A2 | 7/2004 | |
| WO | WO 2012097924 A1 * | 7/2012 | A61B 5/0071 |

OTHER PUBLICATIONS

Selamawit Getachew Kelemu, "Investigation in intra-operative Fluorescence for Microsurgery", Master Thesis, Friedrich Schiller University, Jena, 2012, pp. 0-97.
German Office Action, with translation thereof, for corresponding DE application No. 10 2014 008 243.1 dated Apr. 2, 2015.
Extended European Search Report issued in corresponding European application No. 15 001 596.4 dated Oct. 26, 2015.

* cited by examiner

OPTICAL FILTER SYSTEM AND FLUORESCENCE OBSERVATION SYSTEM

CROSS-REFERENCES TO RELATED APPLICATIONS

The present application claims priority of Patent Application No. 10 2014 008 243.1, filed May 27, 2014 in Germany, the entire contents of which are incorporated by reference herein.

FIELD

The present invention relates to an optical filter system for fluorescence observation, and a fluorescence observation system and a fluorescence observation method using the optical filter system.

BACKGROUND

Fluorescence observation is used in many technical, biological or medical applications in order to visualize various objects such that different types of structures within the object can be distinguished from each other. For this purpose, an illumination light filter is disposed in a beam path between a light source and the object to be observed, and an observation light filter is disposed in a beam path between the object and an eye or a camera detecting images of the object. The illumination light filter allows light to traverse the filter, which excites a fluorescence within the object. The observation light filter allows fluorescent light from the object to traverse the filter. The observation light filter is further configured such that it does not allow light to traverse the filter having wavelengths coinciding with wavelengths of the fluorescent light, which are allowed to traverse the observation light filter. Thus, the light allowed to traverse the observation light filter is substantially only fluorescent light other than illumination light, which has been reflected from or scattered at the object. For this purpose, the illumination light filter blocks substantial portions of the spectrum such that, when the light source is a white light source, the light incident on the object and having traversed the illumination light filter does not allow for an unbiased natural color impression of the object and of, in particular, white regions within the object.

In some situations, the object includes fluorescent regions and non-fluorescent regions, wherein it is desirable to both visualize the fluorescent regions and to allow to perceive the non-fluorescent regions with a substantially natural unbiased or unaltered color impression.

SUMMARY

It is, accordingly, an object of the present invention to provide an optical filter system for fluorescence observation and a fluorescence observation system allowing to perceive non-fluorescent regions of an object with a substantially unaltered color impression.

According to some embodiments of the invention, an optical filter system for fluorescence observation comprises an illumination light filter and an observation light filter which are configured such that they jointly perform their functions. The observation light filter has plural transmitting regions provided for allowing light generated by a fluorescence to traverse the observation light filter such that it can be observed or detected. This means, the transmittance of the observation light filter in dependence of the wavelength has wavelength ranges in which the transmitting regions are provided. The transmitting regions do not overlap, which means that they are separated by blocking regions provided between adjacent transmitting regions. Blocking regions are provided in wavelength ranges in order to block light having wavelengths from within this wavelength ranges and to not allow such light to traverse the observation light filter. Transmitting regions and blocking regions differ with respect to the transmittance of the filter at a given wavelength. At a given wavelength, the transmittance is substantially higher in a given transmitting region than in a blocking region adjacent to the given transmitting region. However, within a same blocking region, or transmitting region, respectively, the transmittance is not required to be constant in dependence of wavelength. The variations of the transmittance within a given transmitting or blocking region are, considerably smaller than changes of transmission between the given transmitting or blocking region and its adjacent blocking region and transmitting region, respectively. The transmittance of the filter at a given wavelength can be defined as usual in the art, i.e. as the inverse of the ratio of the intensity of a beam of light incident on the filter and the intensity of this light traversing the filter. It is possible to characterize the transmittance of a blocking region and the transmittance of a transmitting region by referring to a mean transmittance within that region. In order to determine the mean transmittance of the filter within a given wavelength range, it is possible to determine the transmittance in dependence of the wavelength and to perform an averaging of the measured transmittance over the wavelength range.

The illumination light filter has a blocking region in those wavelength ranges in which the observation light filter has a transmitting region, such that an object illuminated through the illumination light filter does not reflect or scatter light which may traverse the observation light filter at one of its transmitting regions. The light, which is allowed to traverse the observation light filter is then substantially only fluorescent light generated by a fluorescence of the object. In order excite such fluorescence, the illumination light filter has transmitting regions provided for allowing light to traverse the illumination light filter having wavelengths suitable for exciting the fluorescence.

According to some embodiments, the observation light filter has blocking regions at those wavelengths, at which the illumination light filter has transmitting regions.

According to exemplary embodiments, the following relation holds for light from within the wavelength range from 380 nm to 725 nm:

$$\frac{1}{345 \text{ nm}} \int_{380 \text{ nm}}^{725 \text{ nm}} T^O(\lambda) \cdot T^I(\lambda) \, d\lambda < 0.01,$$

wherein $T^O(\lambda)$ is the transmittance of the observation light filter (O) in dependence of the wavelength, and $T^I(\lambda)$ is the transmittance of the illumination light filter (I) in dependence of the wavelength.

This means that light having a wavelength from within the wavelength range from 380 nm to 725 nm may substantially not traverse both filters.

In a fluorescence observation of an object, the object can be illuminated through the illumination light filter, and a fluorescence of the object can be observed or detected with light having traversed the observation light filter. Moreover, it is also possible to directly observe the object and to detect light emerging from the object which has not traversed the observation light filter. Such observation can be performed, for example, using an eye without additional optics, or the observation can be performed using additional optics. Such optics may comprise, for example an ocular provided in a beam path between the object and the eye of a user. Moreover, the optics may image the object onto a camera, which may then obtain images of the object. In such observation or detection of light having not traversed the observation light filter, fluorescence processes in the object are substantially not relevant. The light observed with the eye or detected by a camera is light, which has traversed the illumination light filter and is reflected from or scattered at the object. When the object is illuminated with light having not traversed the illumination light filter, the object appears in its natural colors when it is observed with the eye or when images are detected by a camera. When the object is illuminated with light having traversed the illumination light filter, the object is not illuminated with light having wavelengths at which the illumination light filter has a blocking region. Therefore, the object is not illuminated with white light but with light including a multitude of different wavelengths of the visual light but from which substantial wavelength ranges are missing such that the natural color impression of the object can not be achieved.

For this so reason, the observation light filter does not have only one single transmitting region in order to detect the fluorescence. However, the observation light filter has plural non-overlapping transmitting regions separated by blocking regions of the illumination light filter. The illumination light filter may have a transmitting region at those wavelengths at which the observation light filter has a blocking region in order to illuminate the object with light having wavelengths at which the object emits fluorescent light. Due to the blocking region of the observation light filter, such light does not contribute to the detected fluorescence and serves only for illumination of the object such that it improves the natural color impression when the object is observed without the observation light filter.

The blocking regions of the observation light filter arranged between adjacent transmitting regions of the observation light filter can be advantageously selected for this purpose and such that "gaps" in the illumination light are at least partially "filled". This has the advantage that the color impression generated by the object when it is observed without the observation light filter is improved such that it comes closer to a natural color impression. Herein, generated fluorescent light having wavelengths from within a blocking region of the observation light filter is not detected such that a contrast of the fluorescence image can be reduced since available fluorescent light is not used for the detection of the fluorescence. When the blocking regions of the observation light filter arranged between transmitting regions of the observation light filters are carefully designed, the lack of detected fluorescent light is not significant and compensated by the advantage that the object can be perceived with the natural color impression when it is illuminated with light having traversed the illumination light filter.

According to exemplary embodiments, the illumination light filter has, between 440 nm and 560 nm, a wavelength range of a width greater than 45 nm in which the transmittance of the illumination light filter is smaller than 0.80. This will reduce an amount of green light reaching the object but results in an improved natural color impression of the object in the normal light observation with light having not traversed the observation light filter.

According to exemplary embodiments herein, the wavelength range in which the transmittance is smaller than 0.80 is located between 465 nm and 540 nm. According to further exemplary embodiments, the wavelength range having the width greater than 45 nm has a transmittance smaller than 0.70 and, in particular, smaller than 0.65.

According to exemplary embodiments, an optical filter system for florescence observation comprises an illumination light filter and an observation light filter.

The observation light filter may have the following transmission characteristics in a wavelength range from 380 nm to 725 nm:

The observation light filter has at least two non-overlapping transmitting regions in the wavelength range from 380 nm to 725 nm, wherein each of the at least two transmitting regions of the observation light filter has a mean transmittance greater than a first value between a first wavelength and a second wavelength.

The observation light filter may have plural blocking regions in the wavelength range from 380 nm to 725 nm.

The plural blocking regions of the observation light filter may include a first blocking region of the observation light filter having a mean transmittance smaller than a second value within a wavelength range between 380 nm and a smallest one of the first wavelengths of the at least two transmitting regions of the observation light filter.

The plural blocking regions of the observation light filter may include at least one second blocking region of the observation light filter, wherein each of the at least one second blocking regions of the observation light filter may have a mean transmittance smaller than a third value within a wavelength range between the second wavelength of one transmitting region of the at least two transmitting regions of the observation light filter and the first wavelength of a further transmitting region of the at least two transmitting regions of the observation light filter.

The illumination light filter may have the following transmission characteristics in the wavelength range from 380 nm to 725 nm:

The illumination light filter has plural transmitting regions in the wavelength range from 380 nm to 725 nm.

The plural transmitting regions of the illumination light filter may include a first transmitting region of the illumination light filter having a mean transmittance greater than a fourth value within a wavelength range between 380 nm and a wavelength smaller than the smallest first wavelength of the at least two transmit regions of the observation light filter.

The plural transmitting regions of the illumination light filter may include at least one second transmitting region of the illumination light filter, wherein each of the at least one second transmitting regions may have a mean transmittance greater than a fifth value in a wavelength range between a wavelength greater than the second wavelength of one of the at least two transmitting regions of the observation light filter and a wavelength smaller than the first wavelength of one of the at least two transmitting regions of the observation light filter.

The illumination light filter may have plural blocking regions of the illumination light filter in the wavelength range from 380 nm to 725 nm, wherein a number of the plural blocking regions of the illumination light filter may be equal to a number of the transmitting regions of the observation light filter. Each of the blocking regions of the illumination light filter may have a mean transmittance smaller than a sixth value within a wavelength range between the wavelength which is smaller than the first wavelength of one of the transmitting regions of the observation light filter and the wavelength which is greater than the second wavelength of the one transmitting region of the observation light filter.

According to exemplary embodiments, a number of the plural blocking regions of the observation light filter is equal to a number of the transmitting regions of the observation light filter.

According to further exemplary embodiments, a number of the plural transmitting regions of the illumination light filter is equal to a number of the blocking regions of the observation light filter.

The detection of a fluorescence using an observation light filter having plural transmitting regions separated by blocking regions is particularly suited for the detection of a fluorescence having a broad emission spectrum such that the intensities of the fluorescent light have significant intensities within a broad wavelength range. Such fluorescence may have, for example, a fluorescence spectrum such that the intensities of fluorescent light are greater than 10% of a maximum intensity at all wavelengths within a wavelength range having a width of more than 50 nm or more than 100 nm. Such broad fluorescence spectrum can be divided into plural transmitting regions using the observation light filter, wherein the one or more blocking regions of the observation light filter provided between adjacent transmitting regions of the observation light filter allow for illumination at wavelengths within the blocking regions in order to improve the natural color impression at direct observation with light not having traversed the observation light filter. Herein, it is possible to provide three or more different transmitting regions in the observation light filter which are separated by respective blocking regions. At those wavelengths contained in a blocking region of the observation light filter, the illumination light filter may have corresponding transmitting regions, which improve the natural color impression.

According to embodiments, a fluorescence observation system comprises a light source configured to generate a light beam for illuminating an object region including a fluorescent agent; a first camera configured to detect a fluorescent-light image of the object region; and an optical filter system comprising an observation light filter and an illumination light filter, wherein the illumination light filter is disposed in a beam path between the light source and the object region, wherein the observation light filter is disposed in a beam path between the object region and the first camera, and wherein the optical filter system is the optical filter system according to embodiments as illustrated above.

According to some embodiments, the fluorescence observation system comprises a second camera for detecting a normal-light image of the object region.

According to exemplary embodiments, the fluorescence observation system further comprises a first display configured to display the fluorescent-light image detected by the first camera and the normal-light image detected by the second camera such that the fluorescent-light image and the normal-light image are superimposed with each other.

According to further exemplary embodiments, the fluorescence observation system further comprises imaging optics configured to image the object region, wherein the imaging optics in particular comprises an ocular, wherein, in particular, a second display may be provided and configured to project the fluorescent-light image detected by the first camera into a beam path of the imaging optics.

According to embodiments, a method of performing a fluorescence observation, wherein the method comprises illuminating an object with illumination light traversing an illumination light filter of an optical filter system, wherein the object includes a fluorescent agent; detecting fluorescent light having traversed an observation light filter of the optical filter system, wherein the optical filter system is the optical filter system according to embodiments as illustrated above.

One example of a fluorescence which can be advantageously used in combination with the optical filter system illustrated above is the fluorescence of protoporphyrin IX. This fluorescence is used for visualizing certain types of tumors. The use of the illustrated optical filter system appears to be particularly advantageous for visualizing low-grade gliomas and high-grade gliomas, wherein no other methods are currently known for successfully visualizing low-grade gliomas.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
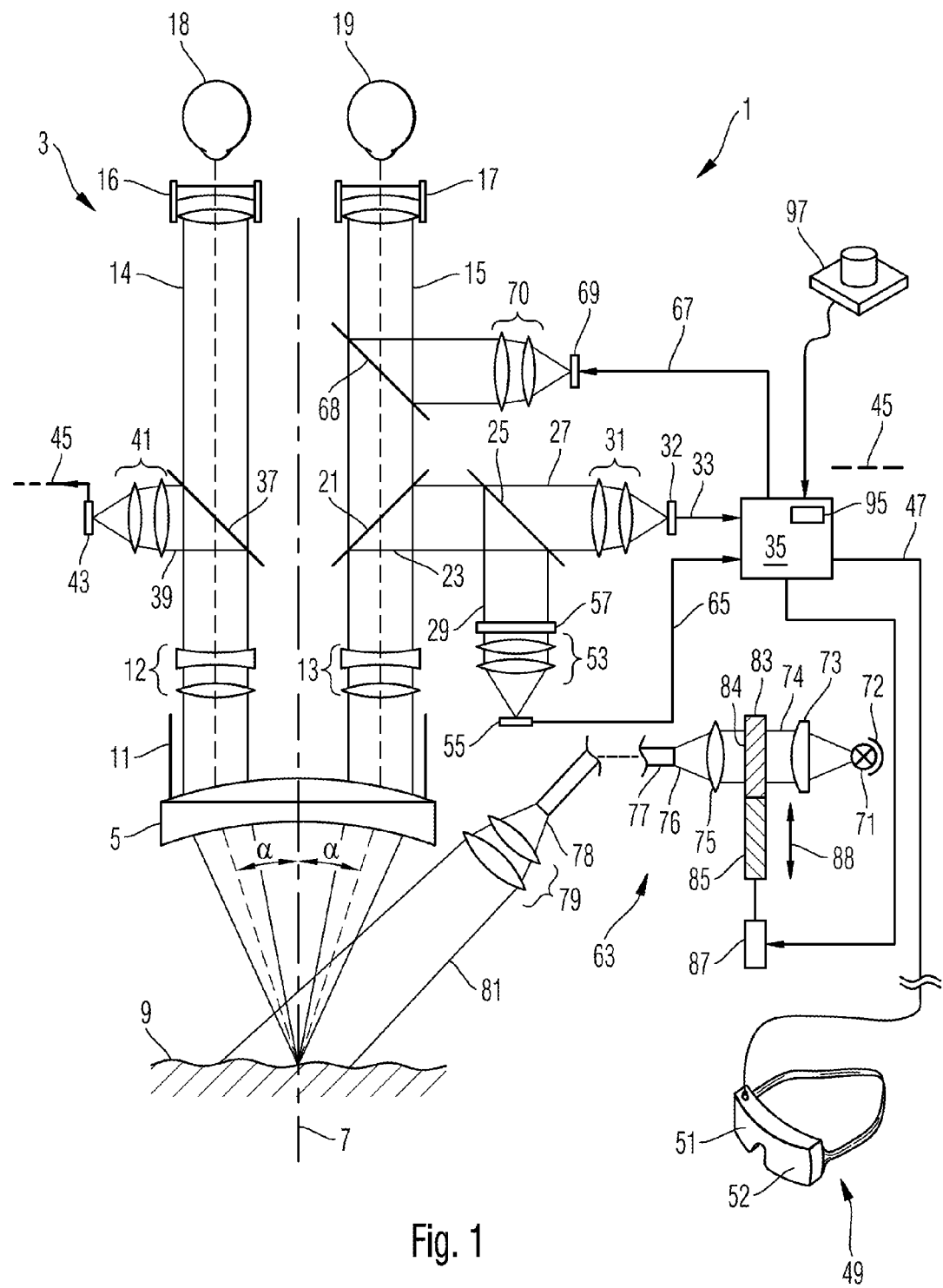
FIG. 1 is a schematic illustration of a fluorescence observation system according to an embodiment.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

An embodiment of a fluorescence observation system will be illustrated with reference to a surgical microscope below. However, embodiments of the fluorescence observation system are not limited to such surgical microscopes and comprise any type of fluorescence observation system in which illumination light directed to the object is filtered using an illumination light filter and in which light emanating from the object is filtered by an observation light filter in order to detect a fluorescence of the object.

The fluorescence observation system and microscope 1 shown in FIG. 1 comprises microscopy optics 3 including an objective lens having an optical axis 7. An object 9 to be inspected is arranged at an object plane of the objective lens 5. Light emanating from the object 9 is formed into an image side beam bundle 11 in which two zoom system 12, 13 are arranged at a distance from the optical axis 7. The zoom systems 12, 13 supply partial beam bundles 14 and 15, respectively, of the image side beam bundle 11 to oculars 16 and 17 via deflecting prisms not shown in FIG. 1. A user may look with his left eye 18 and his right eye 19 into the oculars 16 and 17, respectively, in order to observe a magnified representation of the object 9 as an image.

A semitransparent mirror 21 is arranged in the partial beam bundle 15 for supplying a portion of the light of the beam bundle 15 as a beam 23 to a camera system 24. The camera system 24 may comprise one or more cameras. In the illustrated example, the camera system 24 comprises a camera 32 and a camera 55. Light of the beam 23 having traversed a semitransparent mirror 25 is supplied to the camera 32 via camera adapter optics 31. Light of the beam 23 reflected from the semitransparent mirror 25 is supplied to camera 55 via an observation light filter 57 and camera adapter optics 53. The observation light filter 57 is a fluorescent light filter allowing only fluorescent light emitted from a fluorescent substance in the object to traverse the observation light filter 57 and reach the camera 55. Such observation light filter is not included in the beam path between the object 9 and the camera 32 such that the camera 32 may detect a normal light image of the object 9 while the camera 55 detects a fluorescent light image of the object 9. Images detected by the cameras 32 and 55 are transmitted via data transmission lines 33 and 65, respectively, to a controller 35 which may process the images and store the images in a memory 95.

A semitransparent mirror 37 may similarly be arranged in the other partial beam bundle 14 and supply a beam 39 to camera 43 via camera adapter optics 41. The camera 43 may then detect normal light images of the object 9, which are transmitted via a data line 45 to the controller 35. However, it is also possible that an observation light filter is arranged in a beam path between the object 9 and the camera 43 such that the camera 43 may also detect fluorescent light images if it is desired to detect stereoscopic fluorescent light images. Moreover, it is possible that the light of the beam 39 is supplied to two cameras using a further beam splitter similar to semitransparent mirror 25 such that both stereoscopic normal-light images and stereoscopic fluorescent-light images can be detected.

A display 69 is connected to the controller 35 via a data line 67. An image generated by the controller and displayed on the display 69 is projected into the beam path from the object 9 to the ocular 17 by projection optics 70 and a semitransparent mirror 68 such that the user can see with his eye 19 both the image displayed on display 69 and the direct image of the object 9. Both images are seen in superposition by the eye 19. The controller 35 may display, for example data and information into the ocular, or the controller 35 may display, on the display 69, images detected by the cameras 32, 55 or 43 or images obtained by processing and analyzing images detected by the cameras 32, 55 or 43.

The controller 35 may supply such images also to a head-mounted display 49 via a data line 47, wherein the head-mounted display includes displays 51 and 52 for the right eye and left eye, respectively, of a user.

The microscope 1 further comprises an illumination system 63 configured to generate an illumination light beam 81 directed to the object 9. The illumination system 63 comprises a broad band light source, such as a halogen lamp or xenon lamp 71, a reflector 72 and a collimator 73 for generating a collimated light beam 74 which is directed onto an entrance end 76 of a fiber bundle 77 by plural lenses 75 in order to couple light emitted from the lamp 71 into the fiber bundle 77. The fiber bundle 77 guides the light to an exit end 78 of the fiber bundle 77 located close to the object 9. The light emitted from the exit end 78 is collimated by collimating optics 79 into an illumination light beam 81 directed onto the object 9.

The illumination system 63 further comprises a filter plate 83 including an illumination light filter 84 for fluorescence observation and an illumination light filter 85 for normal-light observation. An actuator 87 controlled by the controller 35 is provided for selectively arranging the illumination light filter 84 for fluorescent light observation or the illumination light filter 85 for normal-light observation in the beam 74 as indicated by an arrow 88 in FIG. 1. The illumination light filter 84 for fluorescent-light observation will be arranged in the beam 74 when it is intended to observe a fluorescence excited in the object 9, while the illumination light filter 85 for normal-light observation will be arranged in the beam 74 if it is intended to observe the object 9 using normal-light, such as white light. The illumination light filter 85 for normal-light observation may be, for example, configured such that infrared light generated by the lamp 71 or light having long wavelength close to infrared light does not traverse the illumination light filter 85 in order to avoid unnecessary warming of the object 9 while visible light of shorter wavelengths may traverse the illumination light filter 85 for illumination of the object 9 such that normal-light observation is possible.

The selective arrangement of one of the illumination light filters 84 and 85 in the beam 74 can be controlled by the user while operating an input device, such as a button 97, connected to the controller 35.

Transmission characteristics of the illumination light filter 84 for fluorescent-light observation and of the observation light filter 57 for fluorescent-light observation are illustrated in more detail with reference to FIG. 2 below.

Figure 2:
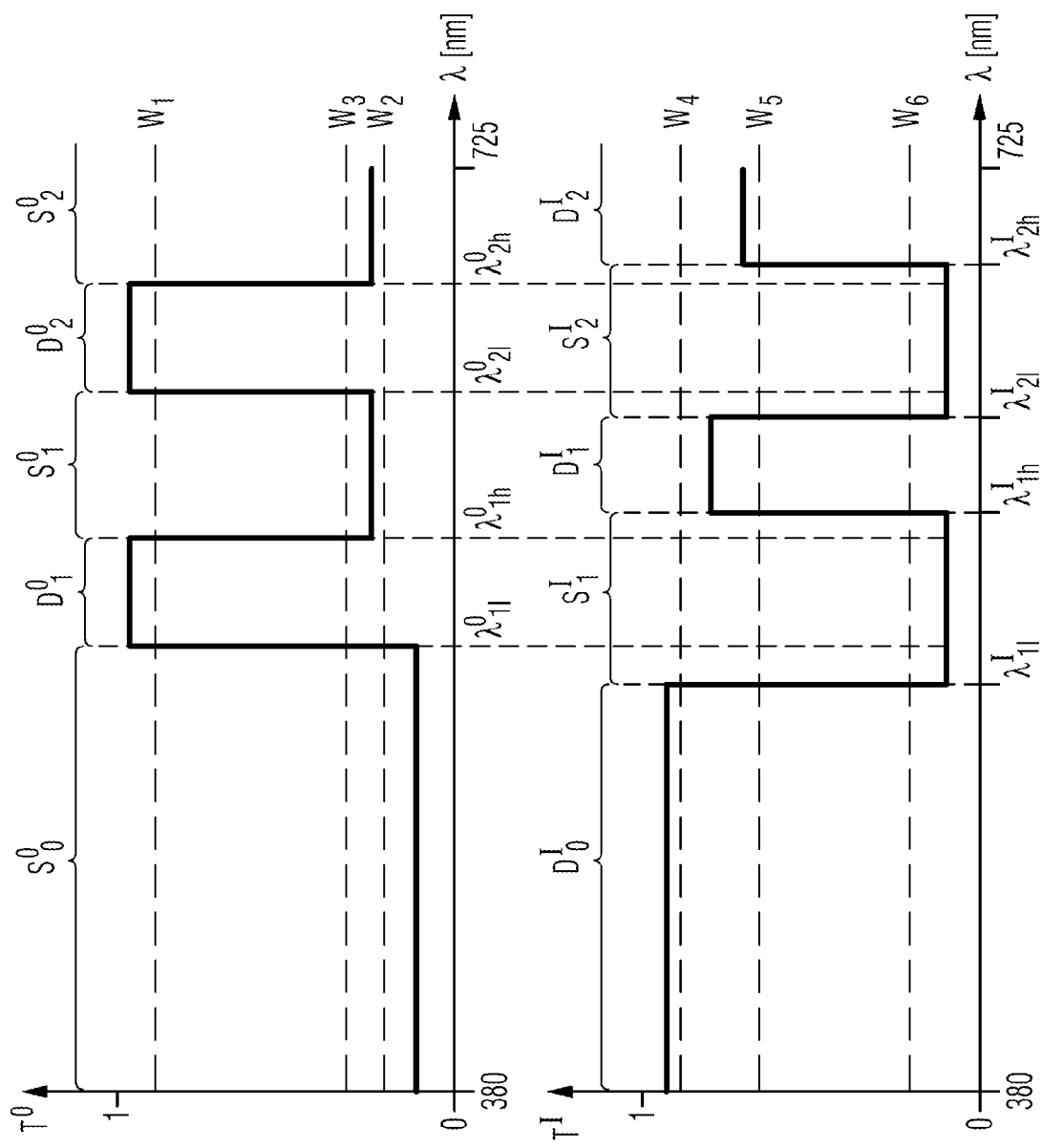
FIG. 2 is a schematic illustration of a transmission characteristics of an observation light filter and of an illumination light filter of an optical filter system according to an embodiment and which can be used in the fluorescence observation system of FIG. 1.

FIG. 2 schematically illustrates the transmission characteristics $T^O$ of the observation light filter 57 in its upper portion, and it schematically illustrates the transmission characteristics $T^I$ of the illumination light filter 84 in its lower portion. In FIG. 2, elements of the observation light filter are indicated with upper index "O" while elements of the illumination light filter are indicated with the upper index "I". The transmission characteristics are illustrated in a wavelength range 380 nm≤λ≤725 nm. In this wavelength range, both filters have plural transmitting regions and blocking regions. The transmitting regions are indicated with the letter "D", and the blocking regions are indicated with the letter "S". The transmitting regions and blocking regions, respectively, are numbered in FIG. 1 from left to right, starting with 0, wherein a lower index added to the letter "D" and "S", respectively, indicates the number of the region.

The transmittance T is low in blocking regions, and the transmittance T is high in transmitting regions. The illustration of FIG. 2 shows sudden changes of the transmittance between transmitting regions and blocking regions. Such sudden changes are shown for illustrative purposes while the change of the transmittance at boundaries between blocking regions and transmitting regions are steady, continuous changes in practice. Wavelengths λ indicating boundaries between blocking regions and transmitting regions are supplemented with a lower index in FIG. 2, wherein a lower index "l" indicates a left boundary of a region and a lower index "h" indicates a right boundary of a region.

The observation light filter is designed to allow fluorescent light to traverse the filter. For this purpose, the illumination light filter comprises two transmitting regions $D_1^O$ and $D_2^O$. The transmission characteristics of the first transmission region has a left edge at a wavelength $\lambda_{1l}^O$ and a right edge at a wavelength $\lambda_{1h}^O$. The second transmission region has a left edge at a wavelength $\lambda_{2l}^O$ and a right edge at a wavelength $\lambda_{2h}^O$. The wavelengths $\lambda_{1l}^O$ and $\lambda_{2h}^O$ are selected such that they are located within the fluorescence spectrum of the observed fluorescence which means that the fluorescent light has significant intensities at and between the wavelength $\lambda_{1l}^O$ and $\lambda_{2h}^O$. The observation light filter has blocking regions at those wavelengths at which it does not have transmitting regions. In the illustration of FIG. 2, the blocking regions are a blocking region $S_0^O$ at wavelengths between 380 nm and $\lambda_{1l}^O$, a further blocking region $S_1^O$ at wavelengths between $\lambda_{1h}^O$ and $\lambda_{2l}^O$, and a still further blocking region $S_2^O$ at wavelengths between $\lambda_{2h}^O$ and 725 nm.

A mean transmittance T can be determined for each of the blocking regions and the transmitting regions. The mean transmittance can be determined by averaging. The averaging can be performed by integration using a suitable formula, such as, for example, the formula $$\overline{T} = \frac{1}{\lambda_{1h}^O - \lambda_{1l}^O} \cdot \int_{\lambda_{1l}^O}^{\lambda_{1h}^O} T(\lambda)\,d\lambda.$$

The mean transmittance of each transmitting region $D^O$ is greater than a value $W_1$. The value $W_1$ can be, for example, greater than 0.7, greater than 0.8, or greater than 0.9. The mean transmittance is smaller than a value $W_2$ in the first blocking region $S_0^O$, and it is smaller than a value $W_3$ in the further blocking regions $S_1^O$ and $S_2^O$. In practice, the first blocking region $S_0^O$ has a substantially greater width than the further blocking regions $S_1^O$ and $S_2^O$ such that the value $W_3$ may be greater than the value $W_2$, such that a significant amount of illumination light does not traverse the illumination light filter. Exemplary values of the value $W_2$ and the value $W_3$ are 0.3, 0.2, and 0.1.

Since the light traversing the transmitting region $D^O$ of the observation light filter should be substantially only fluorescent light, the illumination light filter has blocking regions at those wavelengths at which the observation light filter has transmitting regions. Each transmitting region of the observation light filter has a corresponding blocking region of the illumination light filter. In particular, a blocking region $S_1^I$ of the illumination light filter is associated with the transmitting region $D_1^O$ of the observation light filter, and a blocking region $S_2^I$ of the illumination light filter is associated with the transmitting region $D_2^O$ of the observation light filter. The blocking region $S_1^I$ has a left edge at a wavelength $\lambda_{1l}^I$ and a right edge at a wavelength $\lambda_{1h}^I$, and the blocking region $S_2^I$ has a left edge at a wavelength $\Delta_{2l}^I$ and a right edge at wavelength $\lambda_{2h}^I$. In order to prevent that illumination light may traverse both filters; the blocking regions of the illumination light filter are broader than the corresponding transmitting regions of the observation light filter. In particular: $\lambda_{1l}^I < \lambda_{1l}^O$, $\lambda_{1h}^I > \lambda_{1h}^O$, $\lambda_{2l}^I < \lambda_{2l}^O$ and $\lambda_{2h}^I > \lambda_{2h}^O$.

The illumination light filter has transmitting regions at those wavelengths at which the observation light filter has blocking regions. The transmitting regions of the illumination light filter include a first transmitting region $D_0^I$ between 380 nm and $\lambda_{1l}^I$, a further transmitting region $D_1^I$ between $\lambda_{1h}^I$ and $\lambda_{2l}^I$, and a still further transmitting region $D_2^I$ between $\lambda_{2h}^I$ and 725 nm. The transmittance of the illumination light filter is smaller than a value $W_6$ in the blocking regions and greater than a value $W_4$ in the first transmitting region $D_0^I$ of the illumination light filter. The transmittance of the illumination light filter is greater than a value $W_5$ in the further transmitting regions $D_1^I$ and $D_2^I$. Since, in practice, the transmitting region $D_0^I$ is significantly broader than the further transmitting regions $D_1^I$ and $D_2^I$, the value $W_4$ can be greater than the value $W_5$. Exemplary values of $W_4$ and $W_5$ can be, for example, 0.7, 0.8, and 0.9. Exemplary values of $W_6$ can, for example 0.3, 0.2 and 0.1.

The transmitting region $D_0^I$ has a function of illuminating the object for two different purposes. On the one hand, the light traversing the illumination filter in the transmitting region $D_0^I$ excites the fluorescence such that the corresponding fluorescent light may traverse the observation light filter in the transmission regions $D_1^O$ and $D_2^O$ and to reach the camera 55. The camera 55 may then detect a fluorescence image of the object. On the other hand, the light traversing the illumination light filter in the transmitting region $D_0^I$ illuminates the object for the normal-light observation with light which has not traversed the observation light filter, such that the user may observe the object directly via the oculars 16, 17 with his eyes 18, 19. Moreover, the camera 32 may detect a normal-light image of the object.

If the object were only illuminated with light traversing the illumination light filter in the transmitting region $D_0^I$, the object would appear with a heavily distorted color impression to the eyes 18, 19 of the user since significant portions of the visible spectrum would be missing from the light reaching the eye. A conventional system for fluorescence observation has an illumination light filter having only one single blocking region extending from the wavelength $\lambda_{1l}^I$ to $\lambda_{2h}^I$ in the illustration of FIG. 2. However, the illustrated example shown in FIG. 2 has two blocking regions $S_1^I$ and $S_2^I$ of the illumination light filter, wherein the two blocking regions $S_1^I$ and $S_2^I$ do not overlap and are spaced apart such that the transmitting region $D_1^I$ is arranged between the two blocking regions $S_1^I$ and $S_2^I$. The transmitting region has a function of illuminating the object with additional light for the normal-light observation. When the transmission region $D_1^I$ is carefully selected, such additional light may considerably improve the color impression observed by the eyes such that a white portion of the object appears nearly white. The transmission region $D_1^I$ of the illumination light filter thus provides a significant advantage by improving the color impression of the observed object in a normal light image. As a consequence of the transmitting region $D_1^I$ of the illumination light filter, the observation light filter for fluorescence observation must have the corresponding blocking region $S_1^O$. This results in a reduction of the detectable fluorescent light intensity. Still, the advantage of improving the color impression of the normal-light image is achieved. Also, the further transmitting region $D_2^I$ of the illumination light filter has a function of illuminating the object with light of additional wavelengths in order to improve the color impression for normal light observation.

As mentioned above, the transmission characteristics of the observation light filter and the illumination light filter of FIG. 2 are simplified and provided for illustrative purposes only. In practice, the transmission characteristics can be varied. For example, the transmitting region $D_2^I$ can be omitted such that the blocking region $S_2^I$ is extended to the wavelength of 725 nm. Moreover, the number of transmitting regions $D_1^O$, $D_2^O$) of the observation light filter can be increased, wherein a corresponding higher number of blocking regions $S_1^O$, $S_2^O$, ... of the observation light filter are provided at those wavelengths where the illumination light filter has the transmitting regions $D_1^I$, $D_2^I$, ....

An optical filter system having an illumination light filter and an observation light filter designed for observing a fluorescence of protoporphyrin IX will be illustrated below. The fluorescence of protoporphyrin IX can be used to visualize gliomas. For this purpose, 5-ALA is administered to a patient in advance of a surgery. 5-ALA is a precursor resulting in the desired fluorescence of protoporphyrin IX subsequent to the administration of 5-ALA.

Figure 3:
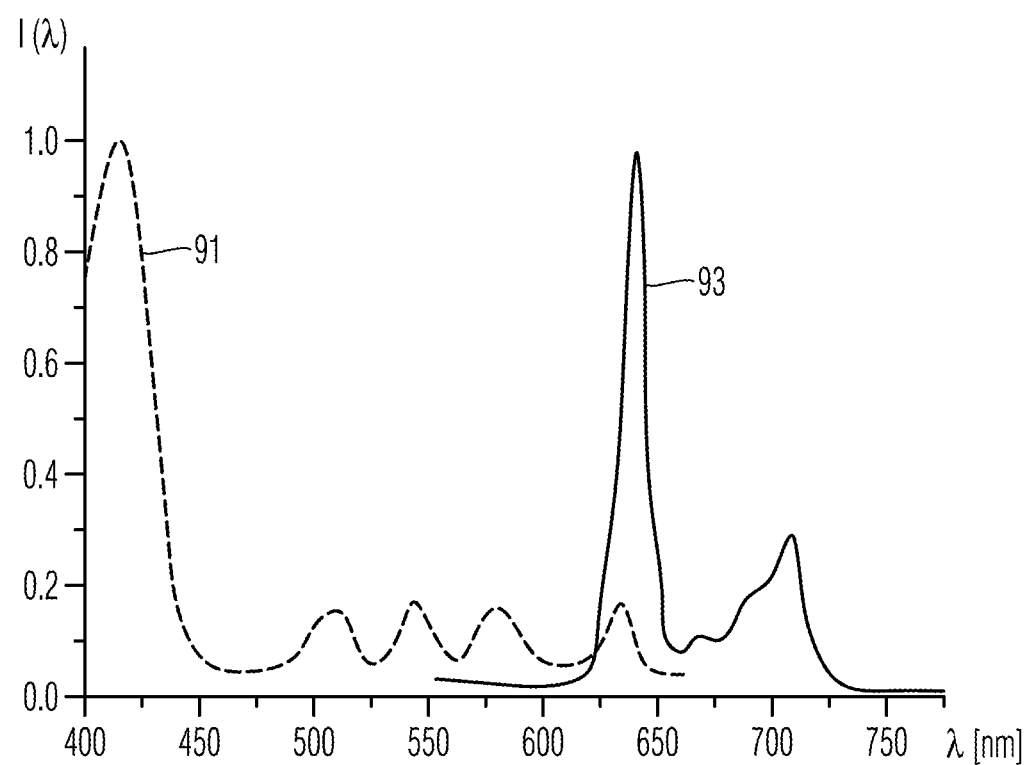
FIG. 3 is a graph showing an excitation spectrum and a fluorescence spectrum of protoporphyrin IX.

FIG. 3 illustrates the fluorescence of protoporphyrin IX for wavelengths from 400 nm to 775 nm. Intensities $I(\lambda)$ of the excitation spectrum of protoporphyrin IX in dependence of the wavelength $\lambda$ are represented by a broken line 91, and intensities $I(\lambda)$ of the emission spectrum of protoporphyrin IX in dependence wavelength $\lambda$ are represented by a full line 93. Both spectra are normalized such that their maximum is 1.0.

Figure 4:
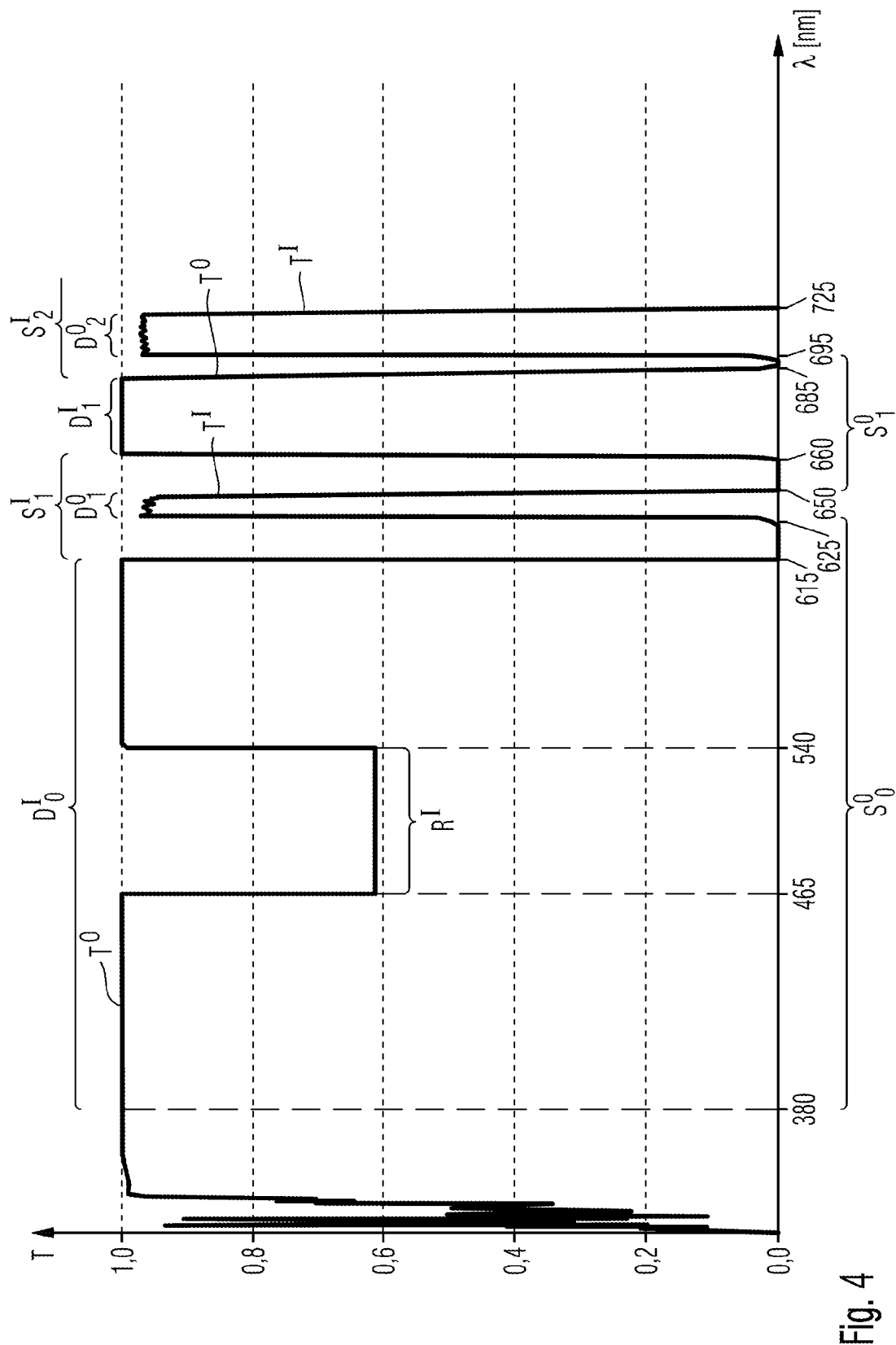
FIG. 4 is a graph showing transmission characteristics of an optical filter system adapted to the fluorescence of protoporphyrin IX.

FIG. 4 shows graphs of transmission characteristics of a filter system designed for observing the fluorescence of protoporphyrin IX. While the transmission of the observation light filter is shown in the upper part of FIG. 2 and the transmission of the illumination light filter is shown in the lower part of FIG. 2, FIG. 4 shows both the transmission characteristic $T^I$ of the illumination light filter and the transmission characteristic $T^O$ of the observation light filter of the filter system in one single graph.

The designations for the transmitting regions and blocking regions of the respective transmission characteristics used in FIG. 4 correspond with those used in FIG. 2.

Reference is made to FIG. 4 below. The observation light filter comprises blocking regions $S_0^O$ and $S_1^O$ and transmitting regions $D_1^O$ and $D_2^O$.

The blocking region $S_0^O$ extends over a wavelength range 380 nm$<\lambda<\lambda_{1l}^O$, wherein $\lambda_{1l}^O=625$ nm.

The transmitting region $D_1^O$ extends over a wavelength range $\lambda_{1l}^O<\lambda<\lambda_{1h}^O$, wherein $\lambda_{1h}^O=650$ nm.

The blocking region $S_1^O$ extends over a wavelength range $\lambda_{1h}^O<\lambda<\lambda_{2l}^O$, wherein $\lambda_{2l}^O=695$ nm.

The transmitting region $D_2^O$ extends over a wavelength range $\lambda_{2l}^O<\lambda<725$ nm.

The illumination light filter comprises transmitting regions $D_0^I$ and $D_1^I$ and blocking regions $S_1^I$ and $S_2^I$.

The transmitting region $D_0^I$ extends over a wavelength range 380 nm$<\lambda<\lambda_{1l}^I$, wherein $\lambda_{1l}^I=615$ nm.

The blocking region $S_1^I$ extends over a wavelength range $\lambda_{1l}^I<\lambda<\lambda_{1h}^I$, wherein $\lambda_{1h}^I=660$ nm.

The transmitting region $D_2^I$ extends over a wavelength range $\lambda_{1h}^I<\lambda<\lambda_{2l}^I$, wherein $\lambda_{2l}^I=685$ nm.

The blocking region $S_2^I$ extends over a wavelength range $\lambda_{2l}^I<\lambda<725$ nm.

The illumination light filter has a further region $R^I$ between 465 nm and 540 nm within the transmitting region $D_0^I$, wherein the transmittance is reduced to a value of about 0.62 in the region $R^I$. This additional region $R^I$ has a function of reducing an amount of green light reaching the object resulting in a further improvement of color impression in the normal light observation.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. An optical filter system for fluorescence observation, wherein the filter system comprises an illumination light filter and an observation light filter;
   wherein the observation light filter has the following transmission characteristics in a wavelength range from 380 nm to 725 nm:
      at least two non-overlapping transmitting regions of the observation light filter, wherein each of the at least two transmitting regions of the observation light filter ranges from a first wavelength to a second wavelength being greater than the respective first wavelength, respectively, and has a mean transmittance greater than a first value within its range, respectively; and
   plural blocking regions of the observation light filter,
   wherein the plural blocking regions of the observation light filter include a first blocking region of the observation light filter, wherein the first blocking region of the observation light filter ranges from 380 nm to a smallest one of the first wavelengths of the at least two transmitting regions of the observation light filter and has a mean transmittance smaller than a second value within its range; and
   wherein the plural blocking regions of the observation light filter include at least one second blocking region of the observation light filter, wherein each of the at least one second blocking regions of the observation light filter adjoins two different transmitting regions of the at least two non-overlapping transmitting regions of the observation light filter, respectively, and has a mean transmittance smaller than a third value within its range, respectively;
   wherein the illumination light filter has the following transmission characteristics in the wavelength range from 380 nm to 725 nm:
      plural transmitting regions of the illumination light filter,
      wherein the plural transmitting regions of the illumination light filter include a first transmitting region of the illumination light filter, wherein the first transmitting region of the illumination light filter ranges from 380 nm to a wavelength smaller than the smallest one of the first wavelengths of the at least two transmitting regions of the observation light filter and has a mean transmittance greater than a fourth value within its range; and
      wherein the plural transmitting regions of the illumination light filter further include at least one second transmitting region of the illumination light filter, wherein each of the at least one second transmitting regions of the illumination light filter is a wavelength range within one of the at least one second blocking regions of the observation light filter, respectively, and has a mean transmittance greater than a fifth value within its range, respectively; and
   plural blocking regions of the illumination light filter,
   wherein each of the plural blocking regions of the illumination light filter is a wavelength range comprising one of the plural transmitting regions of the observation light filter and has a mean transmittance smaller than a sixth value within its range, respectively;
   wherein the first transmitting region of the illumination light filter contains a third transmitting region in a wavelength range between 440 nm and 560 nm having a width greater than 45 nm, wherein the third transmitting region has a mean transmittance less than 0.8; and
   wherein the mean transmittance of the first transmitting region is greater than the mean transmittance of the third transmitting region.

2. The optical filter system according to claim 1, wherein a number of the plural transmitting regions of the illumination light filter is equal to the number of the blocking regions of the observation light filter.

3. The optical filter system according to claim 1, wherein the number of the transmitting regions of the observation light filter is equal two.

4. The optical filter system according to claim 1, wherein the following relation is fulfilled:

$$610 \text{ nm} \leq \lambda_{1l}^{O} \leq 640 \text{ nm},$$

wherein $\lambda_{1l}^{O}$ is the first wavelength of one of the at least two transmitting regions of the observation light filter.

5. The optical filter system according to claim 1, wherein the following relation is fulfilled:

$$10 \text{ nm} \leq \lambda_{1h}^{O} - \lambda_{1l}^{O} \leq 60 \text{ nm},$$

wherein $\lambda_{1l}^{O}$ is the first wavelength and $\lambda_{1h}^{O}$ is the second wavelength of one of the at least two transmitting regions of the observation light filter.

6. The optical filter system according to claim 1, wherein the following relation is fulfilled:

$$680 \text{ nm} \leq \lambda_{2l}^{O} \leq 710 \text{ nm},$$

wherein $\lambda_{2l}^{O}$ is the first wavelength of one of the at least two transmitting regions of the observation light filter.

7. The optical filter system according to claim 1, wherein the following relation is fulfilled:

$$10 \text{ nm} \leq \lambda_{2h}^{O} - \lambda_{2l}^{O} \leq 60 \text{ nm},$$

wherein $\lambda_{2l}^{O}$ is the first wavelength and $\lambda_{2h}^{O}$ is the second wavelength one of the at least two transmitting regions.

\* \* \* \* \*